United States Patent [19]

Miller

[11] Patent Number: 5,834,075
[45] Date of Patent: *Nov. 10, 1998

[54] CORROSION PROTECTION IN CONCRETE SANITARY SEWERS

[75] Inventor: Thomas Michael Miller, Walnut, Calif.

[73] Assignee: PSC Technologies, Inc., King of Prussia, Pa.

[ * ] Notice: This patent issued on a continued prosecution application filed under 37 CFR 1.53(d), and is subject to the twenty year patent term provisions of 35 U.S.C. 154(a)(2).

[21] Appl. No.: 759,412

[22] Filed: Dec. 4, 1996

Related U.S. Application Data

[62] Division of Ser. No. 386,735, Feb. 10, 1995, abandoned.

[51] Int. Cl.$^6$ ................................................. B32B 17/00
[52] U.S. Cl. .................. 428/34.6; 428/34.4; 428/701; 428/702; 428/703; 138/145; 138/146
[58] Field of Search ................................. 428/34.6, 34.4, 428/701, 702, 703; 138/145, 146

[56] References Cited

U.S. PATENT DOCUMENTS

| | | | |
|---|---|---|---|
| 3,080,253 | 3/1963 | Dietz et al. | 117/26 |
| 3,697,322 | 10/1972 | Lee et al. | 117/234 |
| 3,862,851 | 1/1975 | Speirs et al. | 117/70 |
| 4,169,906 | 10/1979 | Hallstrom et al. | 427/183 |
| 4,456,635 | 6/1984 | Albanese et al. | 427/230 |
| 4,615,918 | 10/1986 | Reichert et al. | 427/385.5 |
| 4,668,541 | 5/1987 | Fagerlund | 427/397.7 |
| 4,670,315 | 6/1987 | Hillemeier et al. | 428/36 |
| 4,710,404 | 12/1987 | Reichert et al. | 427/386 |
| 4,786,525 | 11/1988 | Kayser et al. | 427/236 |
| 5,242,708 | 9/1993 | Fekete | 427/136 |
| 5,246,641 | 9/1993 | Perkins et al. | 364/35 |
| 5,525,155 | 6/1996 | Allen | 106/802 |

FOREIGN PATENT DOCUMENTS

| | | |
|---|---|---|
| 1326682 | 4/1963 | France . |
| 424919 | 3/1935 | United Kingdom . |
| 2123516 | 2/1984 | United Kingdom . |

OTHER PUBLICATIONS

Sewer Corrosion Control and Rehabilitation, County Sanitation Districts of Los Angeles County, 5 Pages.
Caustic Spray For Sewer Crown Corrosion Control, by Jamie Baida, 11 Pages.
Microbial Energy Generation/Oxidation of Inorganic Substrates, pp. 158–159.
Preparing Collection Systems for Water Conservation, pp. 52–57, Water Environment & Technology, Aug. 1993.
Metals Meet Their Match, pp. 69–73, Water Environment & Technology, Sep. 1993.
Product Report/Surfactants for household detergents—petrochemical raw materials and uses, pp. 40–41 & 46, C&EN, Jan. 24, 1994.
Generation and Control of Sulfide in Filled Pipes, by Dr. Richard D. Pomeroy, Pomeroy and Associates, Pasadena, Calif., From Sewage and Industrial Wastes, vol. 31, No. 9, 1959.
Process Design Manual for Sulfide Control in Sanitary Sewerage Systems, U.S. Environmental Protection Agency Technology Transfer, Oct. 1974, 9 Pages.

*Primary Examiner*—Timothy Speer
*Attorney, Agent, or Firm*—Ostrolenk, Faber, Gerb & Soffen, LLP

[57] ABSTRACT

A method for protecting concrete surfaces of sanitary sewers includes the steps of providing a concrete surface in a sanitary sewer environment; and coating the concrete surface with magnesium hydroxide or magnesium oxide.

21 Claims, 4 Drawing Sheets

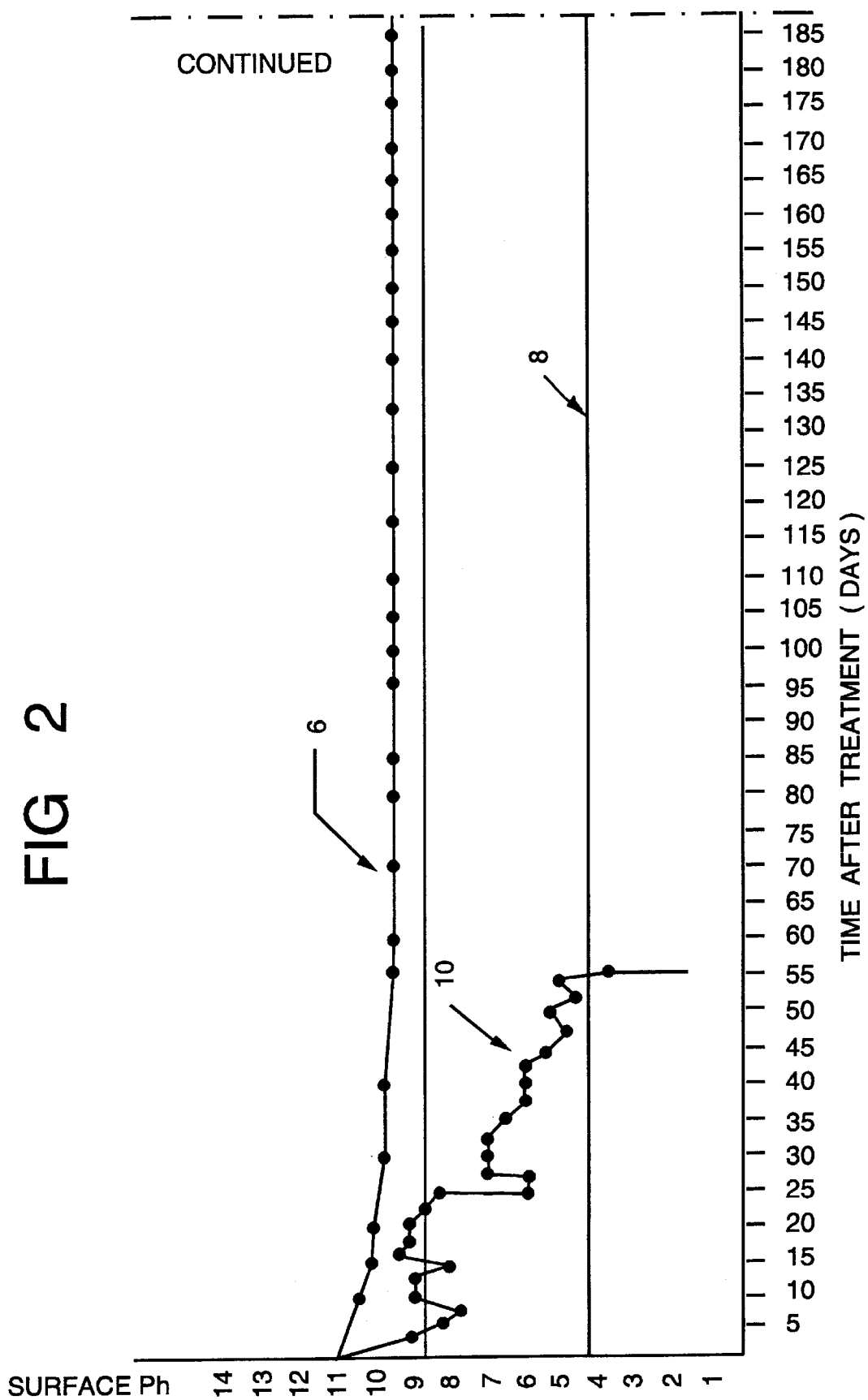

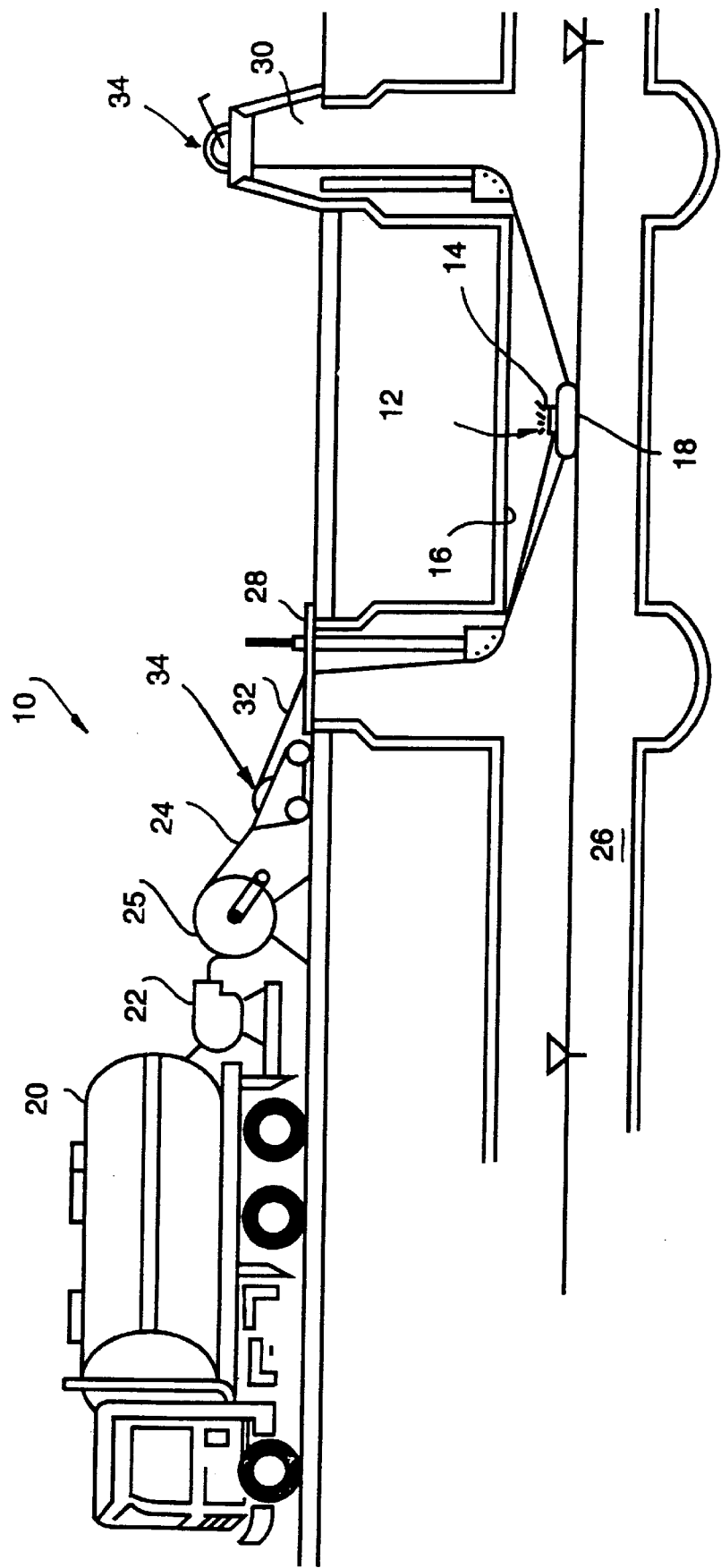

CORROSION PROTECTION IN CONCRETE SANITARY SEWERS

This is a divisional application of application Ser. No. 08/386,735, filed Feb. 10, 1995, now abandoned.

BACKGROUND OF THE INVENTION

1. Field of the Invention

The present invention relates to concrete sewers that are prone to corrosion and more particularly to concrete sewers that are prone to sulfide corrosion.

2. Description of the Prior Art

It has been found that a two step biological process corrodes collection system infrastructures, including concrete sewers and manholes. This is known as "sulfide corrosion", and is increasingly deteriorating today's public works infrastructure.

Sulphide corrosion has detrimental effects on the collection system infrastructure ranging from more frequent odor complaints or potentially lethal atmospheres to failure of collection system pipes and manholes.

In the first step, usually occurring in slow moving sewage below the water line where anaerobic conditions can exist, sulfur reducing anaerobic bacteria, primarily belonging to the genus Desulfovibrio, reduce sulfate ions to sulfide ions. In addition, sulfide can be produced by the bacterial decomposition of protein, and through the decomposition of other organosulfur compounds. However, it is generally recognized that the predominant mechanism for sulfide generation in sewer collection systems is sulfate reduction. Through chemical equilibria, some of the sulfide ions form hydrogen sulfide gas molecules and escape out of the liquid sewage into the headspace atmosphere of the sewer pipe.

In the second step, a different group of sulfur bacteria, primarily belonging to the genus Thiobacillus, establish colonies in the concrete pipe, and through an oxidation process, convert the atmospheric hydrogen sulfide to sulfuric acid with the liberation of free protons and a drop of Ph. The resulting acid attacks the concrete, causing the ultimate destruction of the pipe. It is believed that the acid reacts with the lime in the concrete converting it into a soft putty-like gypsum.

History

Trunk sewers, especially the large diameter lines in the lower reaches of a tributary system, are, for the most part, reinforced concrete pipe. These large sewers generally range in size from 54 inches in diameter up to 144 inches in diameter. In Los Angeles, for example, the oldest of these sewers have been in service for approximately 65 years. At the time these sewers were being designed there were concerns of sulfide corrosion.

To guard against possible sulfide corrosion, the earliest of the large sewers were constructed with vitrified clay liner plates installed on the interior sides and crowns. Vitrified clay, which is used to construct small diameter pipe, is unaffected by sulfuric acid. However, hydrogen sulfide gas and sulfuric acid penetrated between the joints in the tiles and destroyed grouting and cementing materials. By the late 1930's, the practice of using tile liners was discontinued.

Notwithstanding the problems with the tile liners, it was believed that major damage to the structural steel and concrete could be avoided by designing sewers to have sufficient water velocities so that natural aeration forces would minimize the growth of the anaerobic slime layers on the submerged pipe walls where the Desulfovibrio bacteria grow. These natural aeration forces would also help oxidize any sulfide in the water that did form, prior to its being released as hydrogen sulfide gas.

In the early 1950's concrete pipe manufacturers began to market pipes internally lined with plastic to protect against sulfide corrosion. However, at that time there was little data to document how well these plastic liners would remain securely bonded to the concrete and provide effective protection. The cost of the lined pipe was expensive when compared to that of regular, unlined pipe. Consequently, during the 1950's and the 1960's, unprotected reinforced concrete pipe continued to be used. By the mid-1960's sulfide generation was increasing, especially at locations such as pumping plant force mains where depletion of available oxygen occurs.

Research in the late 1960's devised an empirical formula to predict sulfide generation rates and resulting concrete corrosion rates. See report entitled "Sulfide Occurrence and Control In Sewage Collections Systems" which was published in 1983.

In the early to mid-1970's, thorough inspections of concrete sewer lines, for example in Los Angeles, were made in areas where sulfide generation was known to be occurring. Depths of corrosion along the interior crowns of the corresponding sewers were measured. The actual corrosion which was found very closely matched that predicted by the aforementioned formula. Based on the rates of corrosion observed, it then appeared that the remaining structural lives of most of these sewer pipes ranged from at least several decades for the oldest of the sewers, up to hundreds of years for most of the post-World War II sewers. These results were very encouraging, for the normal design life of a major sanitary sewer is assumed to be 100 years.

In the early 1980's, a second thorough inspection of these same sewers were made, and the results were unbelievable: in less than one decade, many of these sewers had experienced significant corrosion to the point where the reinforcing steel was exposed and corroding.

The rate of corrosion had definitely increased and was no longer predictable with the existing empirical formula. The causes of the increased rate of corrosion in the late 1970's and 1980's are not completely understood, but it appears that at least two different factors may have played important roles. First, the institution of limitations on the strength and toxicity of industrial waste waters that could be discharged to the sewers beginning in 1975 and the institution of the U.S. Environmental Protection Agency's Categorical Pretreatment Program for industrial waste discharges in 1983 resulted in significant reduction in discharges of heavy metals to the sewers. These heavy metals played an important role in binding sulfide and preventing the release of hydrogen sulfide to the sewer headspaces and had an inhibitory effect on the Desulfovibrio bacteria. Second, detergent manufacturers employed new formulations for surfactants and brighteners using sulfonated compounds (e.g., linear alkylbenzenesulfonates and derivatives of amsonic acid). Some of these organsulfur compounds may be easily biodegraded into sulfide.

Sulfide and Corrosion Control in Sewers

In the past few years attempts have been made to control the sulfide corrosion problem by attempting to reduce the growth of Desulvovibrio bacteria or to chemically bind up the sulfide which is generated. Research in West Germany, show that the control level for sewer headspace hydrogen sulfide to significantly reduce corrosion is between 1.0 and 3.0 parts per million. This correlates to being able to obtain sufficient control of sulfate reduction to keep the dissolved sulfide concentration in the waste water below 0.1 mg/l. This has proven to be extremely difficult and costly with the conventional methods to chemical control available.

Ferrous and ferric chloride (iron) and liquid caustic soda (sodium hydroxide pH 13–14) are currently being routinely added to selected trunk sewers at a cost of over $3 million per year to attempt to control sulfide generation and corrosion. Iron is added continuously to bind up sulfide as a nonsoluable iron sulfide precipitate.

The caustic soda is added at a semi-weekly frequency to provide a 30 minute, high Ph, shock dose to the Desulvovibrio bacteria. This controls sewer corrosion by neutralizing the sulfuric acid already formed by the bacteria, inactivating and destroying these bacteria, and limiting the formulation of new colonies to prevent the production of acid.

The effectiveness of this treatment program is evaluated by monitoring the concentrations of hydrogen sulfide in the headspaces of the sewers being treated. To date, only modest reductions (50%–60%) have resulted from these treatments, even though significant (75%–95%) dissolved sulfide reductions have been obtained in the waste water. Measurement taken of the surface pH on the crowns of the treated sewers have not changed substantially from their typical acidic values varying between a pH of 1 to 3.

A recent development involves a spray application of a caustic solution, e.g., caustic soda, to the sewer crown. The caustic spray process appears to control micorocrobial formulation of acid on the crown of unprotected reinforced concrete sewer pipe. It is estimated that the operation and maintenance cost to use caustic spray is $0.03 per inch diameter per linear foot of sewer. This compares quite favorably to a sewer rehabilitation cost of $11.00 per inch diameter per linear foot.

Use of caustic soda, however, has several important deficiencies. First, caustic soda is only temporarily effective in halting the progression of crown corrosion. Testing shows that acid producing bacteria are capable of re-establishing themselves in a very short time. The effect of caustic soda spraying is limited to about 60 days.

Caustic soda is a hazardous chemical and is known for its ability to dissolve human flesh. Even a small splash of caustic soda can cause permanent blindness.

When spraying sewer crowns, large above ground hose reels are filled and pressurized with caustic soda. This equipment is often located in residential areas where automobile and pedestrian traffic are common. Traffic accidents, spills, ruptured hoses, valve and pump failures, or operator error represent an unreasonable risk to the safety of both field crews and the public.

The economics of this treatment are subject to frequent variations in the cost and availability of caustic soda. This makes budgeting difficult with chemical costs fluctuating as much as 400% within a one year period.

Last, the treatment must be applied 5 or 6 times per year. This requires a large specially trained group of field technicians to routinely transport, pump, and spray hazardous chemicals in densely populated areas. The long term risks associated with this process may outweigh the benefits.

Rehabilitation

Recently, large sums of money, in Houston, Phoenix, Atlanta and Los Angeles for example, have been expended to rehabilitate or replace many miles of 18" to 144" diameter sewer which have been excessively corroded. All replacement sewers are reinforced concrete with polyvinyl chloride liners cast in place to protect the sewer headspace.

Sliplining of large diameter sewers without diversion of flow presents unique logistic problems regarding control of odors emanating from insertion pits. To provide odor control for ongoing sewer rehabilitation projects, odor control scrubbers are required.

There are still many miles of sewers for which repair or replacement is currently under design in sanitation districts throughout the country. The estimated cost is in the hundreds of millions. There are also many additional miles of sewers which have suffered moderate sulfide corrosion damage, but if the corrosion process is not controlled and continues at its current rate, these sewers will also need to be repaired and replaced in the next 10 years.

The potential for hydrogen sulfide ($H_2S$) generation is expected to increase as more municipalities adopt water conservation programs that include the installation of low-flow plumbing devices. Reduced flows entering collection systems from these water-conserving fixtures is the primary cause. As a result of these reduced flows, collection systems may experience longer retention times in pipes, wet wells, and force mains; increased damming caused by settled solids and grease; and less dissolved oxygen (DO) caused by increased biochemical oxygen demand (BOD).

SUMMARY OF THE INVENTION

It has been found that the corrosion problems described herein may be eliminated or largely diminished by applying magnesium hydroxide and/or magnesium oxide to a concrete surface.

Other features and advantages of the present invention will become apparent from the following description of the invention which refers to the accompanying drawings.

BRIEF DESCRIPTION OF THE DRAWING(S)

For the purpose of illustrating the invention, there is shown in the drawings an embodiment which is presently preferred; it being understood, however, that the invention is not limited by the precise arrangements and instrumentalities shown.

FIG. 3 is the preferred apparatus for spraying magnesium hydroxide and/or magnesium oxide onto a crown of a sanitary sewer.

DETAILED DESCRIPTION OF THE INVENTION

Figure 1:
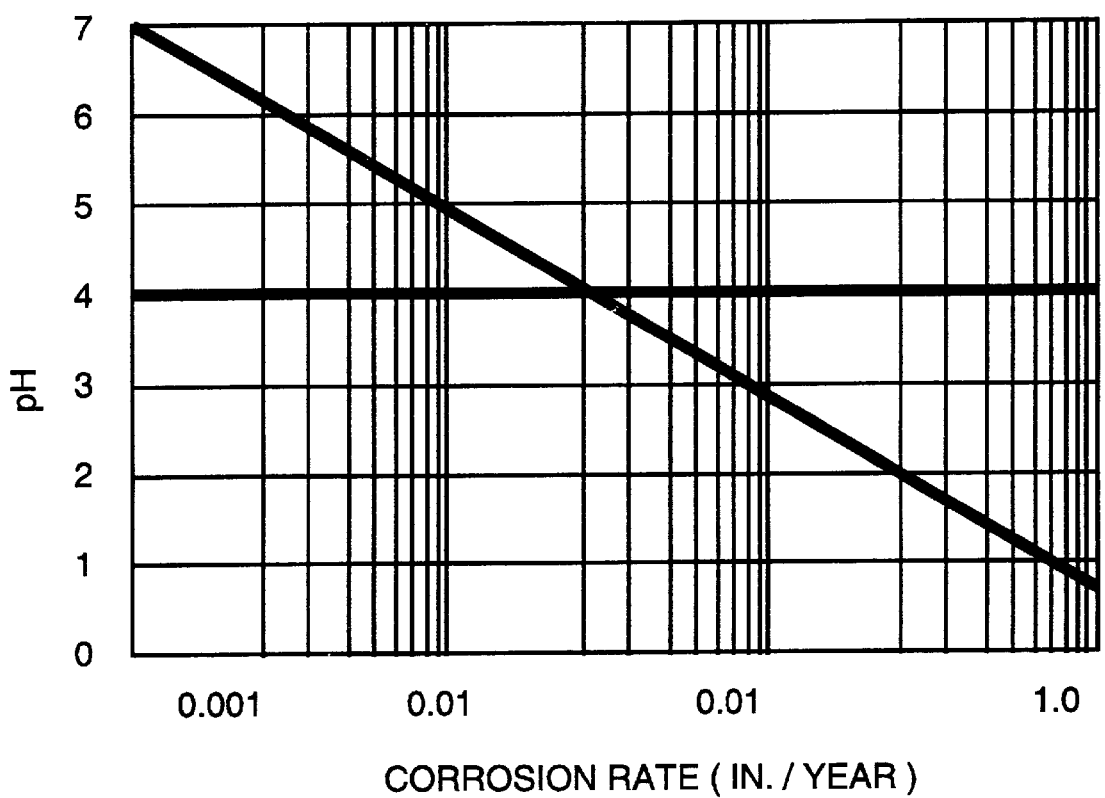
FIG. 1 is a chart showing concrete corrosion rate versus pH.

Due to sulfide corrosion, it has been found that a decrease in surface pH of a concrete sewer of only 2 points, lowers the life expectancy of a collection system crown by a factor of 10, FIG. 1. A ph of the concrete surface above 4 is required to maintain a concrete corrosion rate under an acceptable 0.03"/Year, FIG. 1. At pH 2, concrete corrosion is about a quarter of an inch per year.

In order to control sulfide corrosion, it has been found that applying a layer of magnesium hydroxide ($Mg(OH)_2$), and/ or magnesium oxide (MgO), preferably in the form of a slurry, to concrete surfaces of sanitary sewers prevents corrosion caused by acid. Magnesium hydroxide and/or a magnesium oxide slurry forms a thick, adherent coating of acid neutralizing, relatively insoluble, highly alkaline material sufficient to substantially reduce bacterial density, neutralize acid and discourage further corrosion. Once applied to a concrete sewer surface, the magnesium hydroxide and/or a magnesium oxide raises surface pH on contact and maintains the ph of the concrete surface above 4 for long periods of time after treatment.

Magnesium hydroxide and/or magnesium oxide are superior to other chemicals, including, for example, caustic soda, lime and soda ash for preventing corrosion of concrete sewers in a variety of ways. One eighth inch of magnesium hydroxide, for example, has 100 times less solubility as lime and provides five (5) times the neutralization protection of 200 ml/sqft of 25% caustic soda. More importantly it is much safer. Some other advantages include:

1. Magnesium hydroxide is an insoluble slurry that adheres in a thick layer to unprepared surfaces providing protection that lasts longer than 60 days. It is expected that magnesium hydroxide will provide pH protection for over one year. Caustic soda is a soluble solution and cannot be applied in a thick layer. Caustic soda quickly dissipates permitting acid producing bacteria to return in only 60 days.
2. Magnesium hydroxide has two OH ions and provides higher neutralizing capacity per gram mole. Caustic soda has only one OH ion.
3. Magnesium hydroxide provides more insoluble hydroxyl ions. Therefore, magnesium hydroxide tends to stay in place rather than rinsing away with splashing water. Hydroxyl ions in caustic soda are dissociated.
4. Magnesium hydroxide produces a safe soluble reactant with very little sludge. Sludge from neutralization of acid by caustic soda is gelatinous and contributes to sludge.
5. Magnesium hydroxide requires no placarding or special handling and presents no chemical hazard to the environment, users, or the public. Caustic soda is hazardous requires D.O.T. truck placards.
6. Magnesium hydroxide adds little mechanical loading to corroded structures.
7. Magnesium hydroxide is white allowing easy inspection ensuring complete coverage. Caustic soda is a clear liquid which is difficult to see on the treated surface.
8. Magnesium hydroxide is soft, preventing egg shelling and blockage of sewers.
9. Magnesium hydroxide may be pumped long distances.
10. Magnesium hydroxide passes through small diameter spray nozzles.
11. Magnesium hydroxide has the lowest annualized installed cost versus other surface treatments.
12. Magnesium hydroxide has sufficient pH to kill or disable acid producing bacteria.
13. Sanitation districts have used dusted lime in the past to control crown corrosion however $CO_2$ levels in the headspace quickly carbonate lime rendering it ineffective. Further, past practice has taught that sludge generated from lime treatment is high in volume and weight often generating eight (8) times as much sludge as the amount of lime added eliminating the material cost advantage of lime.

Figure 2:
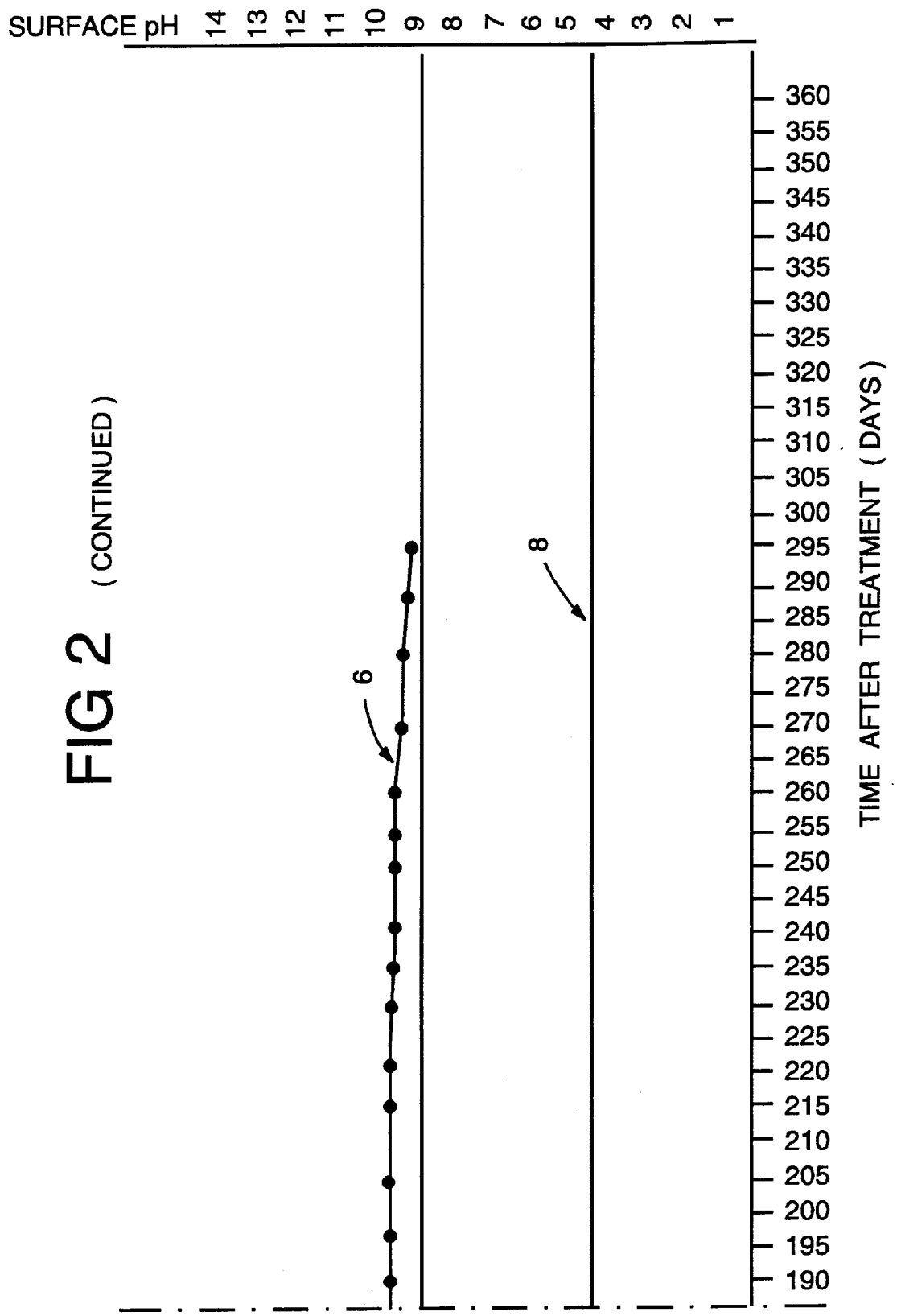
FIG. 2 is a chart showing concrete surface pH versus days following spray treatment.

FIG. 2 shows the results of a representative crown spraying field trial comparing caustic soda and magnesium hydroxide. It can be seen that the pH of a concrete surface 6 sprayed with magnesium hydroxide, having approximately 50% solids content, 450 ml/Sqft 50% Thioguard $Mg(OH)_2$) maintained a surface pH above the corrosion threshold (pH 4) for almost one year. Additional testing indicates that magnesium hydroxide will maintain the surface pH above the corrosion threshold for over one year. In contrast, it has been found that the pH of a concrete surface 10 sprayed with a 25% solution of caustic soda 200 ml/sqft 25% NaOH, dipped below the corrosion threshold 8 (pH 4) only after about sixty (60) days.

Magnesium hydroxide and/or magnesium oxide rely on two phenomena to be effective. First they have a pH near 10.5, which while safe to humans is just above the tolerance of common acid producing bacteria to kill or disable them. Small amounts of lime (calcium hydroxide) can be added to magnesium hydroxide and/or magnesium oxide slurry to increase the pH and enhance the slurry's ability to kill bacteria. It is anticipated that other biocides or hardening agents such as sodium silicate, sodium bisulfate, magnesium sulfate, magnesium chloride, phosphates, or other materials intended to impart mechanical strength, may be added to further enhance its performance.

Secondly, as the bacteria re-establishes, alkalinity provided by the magnesium hydroxide and/or magnesium oxide neutralize acids produced by the bacteria producing a soluble, tightly bonded sulfate and prevents rapid re-establishment of bacteria. This prevents low pH necessary for the really aggressive acidifiers. The magnesium hydroxide and/or magnesium hydroxide slurry is sacrificial and protects the cement which bonds concrete.

A magnesium hydroxide and/or magnesium oxide slurry can be prepared by adding caustic calcined magnesium oxide (MgO), preferably in a dry powder form, to water. The magnesia can be obtained from any of the known suppliers including, Premier Services Corporation, King of Prussia, Pa. Premier Services sells magnesia in dry powder form under the trademark MAGOX®.

When magnesium oxide is added to water it undergoes hydration and converts to magnesium hydroxide. The rate of this reaction can be varied depending upon the surface area of the MgO, starting water temperature, vessel configuration, and agitation. Either a slowly hydrating MgO, or a fully hydrated $Mg(OH)_2$ slurry may be applied to the concrete surface.

A magnesium hydroxide slurry can also be purchased by any of the known suppliers, including Premier Services who sells magnesium hydroxide slurry under the trademark AQUAMAG®.

In a preferred embodiment, a specially hydrated and formulated slurry, marketed by Premier Services Corporation under the trademark THIOGUARD™, is used in sanitary sewers as an acid acceptor. THIOGUARD™ offers a safe, economic alternative reagent for acid neutralization and water treatment and has been found to be particularly effective in extending the useful life of concrete sewer crowns and manholes by neutralizing harmful sulfuric acid.

THIOGUARD™ is an off-white slurry composed predominantly of agglomerated magnesium hydroxide particles and is made from hydrated calcined natural magnesite or precipitated from sea water, bitterns, or brines. Table I, below, depicts a typical chemical analysis of THIOGUARD on a loss free basis.

TABLE I

| Chemical Analysis, Wt % (loss free basis) | Typical | Maximum | Minimum |
|---|---|---|---|
| MgO | 93–98 | 98.5 | 92.0 |
| CaO | .5–2.5 | 3.5 | — |
| $R_2O_3$ | .5–1.5 | — | — |
| Insolubles | .5–3.0 | — | — |
| Viscosity, cps | 500–10,000 | — | — |
| Density, lb/gal | 11.8 | — | — |
| % Solids by Wt % | 50 | 55 | 45 |

The component $R_2O_3$ refers to natural impurities such as $Al_2O_3$ and $Fe_2O_3$ that are indigenous to ore bodies. The insolubles include, for example, $SiO_2$, $MgCO_3$ and $CaCO_3$.

In a preferred embodiment, the magnesium hydroxide or magnesium oxide in the form of a slurry is sprayed on the inside crown portion of a sewer pipe from the water line up. Preferably, the spray delivery system is similar to that used to apply a caustic solution to the inside of a sewer line.

It should be realized by those skilled in the art that the magnesium hydroxide and/or magnesium oxide can be applied to any other concrete surface that is subject to sulfide corrosion or the like, e.g., a manhole, or by any method in any form, e.g., dry powder form or the like.

Referring now to FIG. 3, the basic spray system 10 consists of a spray head assembly 12 fitted with two or three fan type airless spray nozzles 14 arranged to provide full coverage of the surface to be treated 16. The nozzles 14 are mounted on a collapsible spray head float 18. A supply tanker 20 delivers the magnesium hydroxide to a chemical pump 22, such as a pneumatic or hydraulic powered GRACO 10:1, and pumps the magnesium hydroxide through a high pressure hose 24 mounted on a hose reel 25.

The spray head float 18 is pulled through the sewer 26 between manholes 28 and 30, for example, using a cable 32 and one or more electrically driven cable winch 34 by which the travel speed of the float 18 is controlled. Operators up and downstream communicate by radio to monitor the hose and spray head float 18 progress. The correct spray head float speed is determined by the rate of flow of magnesium hydroxide to the nozzles 14.

The spray head 12 is constructed of a 12 inch section of 4 inch diameter PVC pipe with end caps. One end is fitted with a quick disconnect caustic feed nipple, not shown. Preferably, there are three 316 stainless steel, clog-free, whirl type nozzles 14 with a full cone, 90° angle spray pattern. The nozzles 14 are mounted diagonally across the top of the spray head 12 at a 45° angle to the horizontal axis at equal distances apart to achieve full coverage of the sewer crown area 16 above the sewage surface. The nozzles 14 can spray up to 2.4 gallons per minute at 40 psi.

The spray head float 18 consists of three 4 inch diameter, 60 inch long PVC tubes connected in parallel by two adjustable arms on each side, not shown. The adjustable arms allow the outside tubes to be moved away from, or closer to, the center tube to accommodate different size sewers flowing at various depths. The float 18 can be pulled forward or backward, which gives the spray operation maximum flexibility. It also enables the crew to remove the float from the sewer if an emergency occurs.

The pulling equipment consists of two identical electrical cable winches 34 (one positioned at each manhole) and are used to facilitate the spray operation. The cable winch frame is made of lightweight aluminum for ease of handling. One of the two winches 34 is used to pull and control the speed of the float 18. The second winch is connected to the float 18 for emergency purposes. Preferably, each winch 34 has a 2,500 foot length of ⅛ inch diameter, stainless steel cable to allow for treatment of more than one sewer section without moving the float from the sewer.

The power source for the equipment is provided by two portable generators, one rated at 3.3 kilowatts and the other at 6.5 kilowatts, not shown. The 6.5 kilowatts generator is used to provide power to the pump motor, one cable winch in the motor operator for the hose reel. The 3.3 kilowatt generator is used to power the pulling equipment at the other end of the sewer section being treated.

The viscosity of the magnesium hydroxide and/or magnesium oxide slurry can be varied to provide the optimum sprayability and pumping characteristics and achieve different degrees of surface adhesion to the concrete. Preferably, the slurry should have a viscosity to allow pumping while enhancing adhesion and discouraging runoff. It has been found that viscosity's ranging between 500 and 5000 centipoise (cps), preferably 2000 cps, provide the widest range of application.

The viscosity and the properties of the slurry can be varied by any of the known methods including changes in the solids to water ratio, or by the use of polymers to enhance or alter these properties as desired for differing field conditions or equipment configurations, e.g., increasing or decreasing the water content or by adding in more magnesia powder.

It is recommended that once applied to a concrete surface, the slurry should include at least 30%, preferably at least 50%, by weight magnesium oxide or magnesium hydroxide. For best results, the magnesium hydroxide slurry should be applied to the concrete surface to result in a layer approximately 0.0625 to 0.25 inches thick.

A related chemistry for this application addresses varying water level. Magnesium oxide mixed with sodium silicate produces a slurry which, when dried, yields a hard alkaline material composite of unhydrated magnesium oxide encapsulated in sodium silicate. Acid produced by surface bacteria is neutralized by the sodium silicate. As the sodium silicate dissolves, magnesium oxide is exposed which dehydrates the bacteria and also neutralizes.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A corrosion resistant sewer, comprising:
   a concrete sewer line having an interior surface; and
   a magnesium oxide layer made substantially of magnesium oxide deposited on at least a portion of the interior surface.

2. The corrosion resistant sewer of claim 1, wherein the magnesium oxide layer is approximately 0.0625 to 0.25 inches thick.

3. The corrosion resistant sewer of claim 1, wherein the interior surface of the concrete sewer line includes a crown portion, and wherein the magnesium oxide layer is deposited on the crown portion.

4. The corrosion resistant sewer of claim 1, wherein the magnesium oxide layer comprises sodium silicate so that when dry, the layer is a hard alkaline material composite of unhydrated magnesium oxide encapsulated in sodium silicate.

5. The corrosion resistant sewer of claim 1, wherein the magnesium oxide layer comprises:

| Chemical Analysis (loss free basis) | Wt. % |
|---|---|
| MgO | about 92–98% |
| CaO | about .5–3.5% |
| % solids by wt % | about 45–55. |

6. The corrosion resistant sewer of claim 1, wherein the magnesium oxide layer includes at least about 30–50% magnesium oxide.

7. The corrosion resistant sewer of claim 1, wherein the magnesium oxide layer is deposited as a slurry.

8. The corrosion resistant sewer of claim 7, wherein the slurry has a viscosity between about 500 and 5000 centipoise.

9. The corrosion resistant sewer of claim 8, wherein the slurry has a viscosity of about 2000 centipoise.

10. The corrosion resistant sewer of claim 7, wherein the slurry includes a hydrating magnesium oxide.

11. The corrosion resistant sewer of claim 1, wherein the pH of the interior surface is at least approximately 4 after the magnesium oxide layer is formed on the interior surface.

12. A corrosion resistant sewer, comprising:
   a concrete sewer line having an interior surface; and
   a magnesium hydroxide layer made substantially of magnesium hydroxide deposited on at least a portion of the interior surface.

13. The corrosion resistant sewer of claim 12, wherein the magnesium hydroxide layer is approximately 0.0625 to 0.25 inches thick.

14. The corrosion resistant sewer of claim 12, wherein the interior surface of the concrete sewer line includes a crown portion, and wherein the magnesium hydroxide layer is deposited on the crown portion.

15. The corrosion resistant sewer of claim 12, wherein the magnesium hydroxide layer comprises sodium silicate so that when dry, the layer is a hard alkaline material composite of magnesium hydroxide encapsulated in sodium silicate.

16. The corrosion resistant sewer of claim 12, wherein the magnesium hydroxide layer comprises:

| Chemical Analysis (loss free basis) | Wt. % |
|---|---|
| $Mg(OH)_2$ | about 92–98% |
| CaO | about .5–3.5% |
| % solids by wt % | about 45–55. |

17. The corrosion resistant sewer of claim 12, wherein the magnesium hydroxide layer includes at least about 30–50% magnesium hydroxide.

18. The corrosion resistant sewer of claim 12, wherein the magnesium hydroxide layer is deposited as a slurry.

19. The corrosion resistant sewer of claim 18, wherein the slurry has a viscosity between about 500 and 5000 centipoise.

20. The corrosion resistant sewer of claim 19, wherein the slurry has a viscosity of about 2000 centipoise.

21. The corrosion resistant sewer of claim 12, wherein the pH of the interior surface is at least approximately 4 after the magnesium hydroxide layer is formed on the interior surface.

* * * * *